US 8,795,163 B2

(12) United States Patent
Widenhouse et al.

(10) Patent No.: US 8,795,163 B2
(45) Date of Patent: Aug. 5, 2014

(54) INTERLOCKING SEAL COMPONENTS

(75) Inventors: Tamara S. V. Widenhouse, Clarksville, OH (US); Jerome R. Morgan, Cincinnati, OH (US); Charles J. Scheib, Loveland, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 810 days.

(21) Appl. No.: 12/479,096

(22) Filed: Jun. 5, 2009

(65) Prior Publication Data

US 2010/0312060 A1   Dec. 9, 2010

(51) Int. Cl.
*A61B 1/32* (2006.01)

(52) U.S. Cl.
USPC ....... 600/201; 600/204; 600/206; 604/167.01

(58) Field of Classification Search
USPC ........ 600/184–246; 604/167.01–167.04, 246, 604/256, 264, 278
See application file for complete search history.

(56) References Cited

U.S. PATENT DOCUMENTS

| 2,129,391 A | 9/1938 | Wappler |
| 3,402,710 A | 9/1968 | Paleschuck |
| 3,654,965 A | 4/1972 | Gramain |
| 4,112,932 A | 9/1978 | Chiulli |
| 4,306,545 A | 12/1981 | Ivan et al. |
| 4,379,458 A | 4/1983 | Bauer et al. |
| 4,402,683 A | 9/1983 | Kopman |
| 4,417,888 A | 11/1983 | Cosentino et al. |
| 5,010,925 A | 4/1991 | Atkinson et al. |
| 5,091,435 A | 2/1992 | Suzuki et al. |
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |

(Continued)

FOREIGN PATENT DOCUMENTS

| DE | 19814576 A1 | 10/1999 |
| DE | 20022005 U1 | 4/2001 |

(Continued)

OTHER PUBLICATIONS

International Search Report and Written Opinion for International App. No. PCT/US2010/036811 dated Sep. 14, 2010 (6 pages).

(Continued)

*Primary Examiner* — Cris L Rodriguez
*Assistant Examiner* — Edward Moran

(57) ABSTRACT

Methods and devices are provided to allow for easy customization of a surgical access device by an end user. In one exemplary embodiment a surgical access device is provided that includes a plurality of elongate seal elements that are configured to form a sealed configuration between a surgical site and an outside environment. The seal elements can be disposed in a surgical opening and can mate directly to each other with the outermost seal elements mating directly to tissue of the opening. The seal elements can include one or more mating elements to provide the desired mating. The seal elements can also include sealable openings that are configured to receive surgical instruments for use at the surgical site. The sealable openings maintain the desired seal throughout the course of a surgical procedure. Exemplary methods for providing custom configurations on location are also provided.

17 Claims, 7 Drawing Sheets

(56) References Cited

U.S. PATENT DOCUMENTS

| | | |
|---|---|---|
| 5,209,741 A | 5/1993 | Spaeth |
| 5,235,966 A | 8/1993 | Jamner |
| 5,269,772 A * | 12/1993 | Wilk ........................... 604/284 |
| 5,308,336 A | 5/1994 | Hart et al. |
| 5,312,417 A | 5/1994 | Wilk |
| 5,320,611 A | 6/1994 | Bonutti et al. |
| 5,342,315 A | 8/1994 | Rowe et al. |
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,395,342 A * | 3/1995 | Yoon ........................ 604/167.03 |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,531,758 A | 7/1996 | Uschold et al. |
| 5,545,179 A | 8/1996 | Williamson, IV |
| 5,562,677 A | 10/1996 | Hildwein et al. |
| 5,569,205 A | 10/1996 | Hart et al. |
| 5,569,254 A | 10/1996 | Carlson et al. |
| 5,584,850 A | 12/1996 | Hart et al. |
| 5,628,732 A | 5/1997 | Antoon, Jr. et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,653,718 A | 8/1997 | Yoon |
| 5,672,168 A | 9/1997 | de la Torre et al. |
| 5,676,657 A | 10/1997 | Yoon |
| 5,695,448 A | 12/1997 | Kimura et al. |
| 5,707,359 A | 1/1998 | Bufalini |
| 5,752,970 A | 5/1998 | Yoon |
| 5,782,812 A | 7/1998 | Hart et al. |
| 5,797,888 A | 8/1998 | Yoon |
| 5,803,919 A | 9/1998 | Hart et al. |
| 5,814,058 A | 9/1998 | Carlson et al. |
| 5,827,319 A | 10/1998 | Carlson et al. |
| 5,843,040 A | 12/1998 | Exline |
| 5,865,807 A | 2/1999 | Blake, III |
| 5,868,762 A | 2/1999 | Cragg et al. |
| 5,882,344 A | 3/1999 | Stouder, Jr. |
| 5,891,013 A | 4/1999 | Thompson |
| 5,899,208 A | 5/1999 | Bonadio |
| 5,906,577 A | 5/1999 | Beane et al. |
| 5,946,280 A | 8/1999 | Ohkubo |
| 5,957,913 A | 9/1999 | de la Torre et al. |
| 5,990,382 A | 11/1999 | Fox |
| 5,997,515 A * | 12/1999 | de la Torre et al. ............ 604/256 |
| 6,024,736 A | 2/2000 | de la Torre et al. |
| 6,033,426 A * | 3/2000 | Kaji ........................... 606/213 |
| RE36,702 E | 5/2000 | Green et al. |
| 6,056,766 A | 5/2000 | Thompson et al. |
| 6,066,090 A | 5/2000 | Yoon |
| 6,077,288 A | 6/2000 | Shimomura et al. |
| 6,080,174 A | 6/2000 | Dubrul et al. |
| 6,086,603 A | 7/2000 | Termin et al. |
| 6,120,513 A | 9/2000 | Bailey et al. |
| 6,123,689 A | 9/2000 | To et al. |
| 6,142,396 A | 11/2000 | Gallus |
| 6,142,936 A | 11/2000 | Beane et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,348,034 B1 | 2/2002 | Thompson |
| 6,352,503 B1 | 3/2002 | Matsui et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,488,620 B1 | 12/2002 | Segermark et al. |
| 6,551,270 B1 * | 4/2003 | Bimbo et al. .............. 604/93.01 |
| 6,551,282 B1 | 4/2003 | Exline et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,163,525 B2 | 1/2007 | Franer |
| 7,214,185 B1 | 5/2007 | Rosney et al. |
| 7,229,408 B2 | 6/2007 | Douglas et al. |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,449,011 B2 | 11/2008 | Wenchell et al. |
| 7,481,795 B2 | 1/2009 | Thompson et al. |
| 2002/0156432 A1 | 10/2002 | Racenet et al. |
| 2003/0028179 A1 | 2/2003 | Piskun |
| 2003/0139756 A1 | 7/2003 | Brustad |
| 2003/0216770 A1 | 11/2003 | Persidsky et al. |
| 2004/0015185 A1 | 1/2004 | Ewers et al. |
| 2004/0019322 A1 | 1/2004 | Hoffmann |
| 2004/0082969 A1 | 4/2004 | Kerr |
| 2004/0106942 A1 | 6/2004 | Taylor et al. |
| 2004/0117032 A1 | 6/2004 | Roth |
| 2004/0138528 A1 | 7/2004 | Richter et al. |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 | 9/2005 | Hart et al. |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |
| 2006/0030755 A1 | 2/2006 | Ewers et al. |
| 2006/0071432 A1 | 4/2006 | Staudner |
| 2006/0129165 A1 | 6/2006 | Edoga et al. |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1 | 11/2006 | Bonadio et al. |
| 2006/0247500 A1 | 11/2006 | Voegele et al. |

(56) References Cited

U.S. PATENT DOCUMENTS

| | | |
|---|---|---|
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088204 A1 | 4/2007 | Albrecht et al. |
| 2007/0088258 A1 | 4/2007 | Wenchell et al. |
| 2007/0088277 A1 | 4/2007 | McGinley et al. |
| 2007/0118021 A1 | 5/2007 | Pokorney |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0208312 A1 | 9/2007 | Norton et al. |
| 2007/0255219 A1 | 11/2007 | Vaugh et al. |
| 2008/0009797 A1 | 1/2008 | Stellon et al. |
| 2008/0025519 A1 | 1/2008 | Yu et al. |
| 2008/0027476 A1 | 1/2008 | Piskun |
| 2008/0051739 A1 | 2/2008 | McFarlane |
| 2008/0058728 A1 | 3/2008 | Soltz et al. |
| 2008/0065021 A1 | 3/2008 | Jenkins et al. |
| 2008/0086080 A1 | 4/2008 | Mastri et al. |
| 2008/0119821 A1 | 5/2008 | Agnihotri et al. |
| 2008/0132765 A1 | 6/2008 | Beckman et al. |
| 2008/0255519 A1 | 10/2008 | Piskun et al. |
| 2008/0281161 A1 | 11/2008 | Albrecht et al. |
| 2009/0005799 A1 | 1/2009 | Franer et al. |
| 2009/0082731 A1 | 3/2009 | Moreno |
| 2009/0118587 A1 | 5/2009 | Voegele et al. |
| 2009/0187079 A1 | 7/2009 | Albrecht et al. |
| 2009/0227843 A1* | 9/2009 | Smith et al. .................... 600/208 |
| 2009/0270685 A1 | 10/2009 | Moreno et al. |
| 2009/0270686 A1 | 10/2009 | Duke et al. |
| 2009/0270818 A1 | 10/2009 | Duke |
| 2010/0010310 A1 | 1/2010 | Weisenburgh, II et al. |
| 2010/0081863 A1 | 4/2010 | Hess et al. |
| 2010/0081864 A1 | 4/2010 | Hess et al. |
| 2010/0081871 A1 | 4/2010 | Widenhouse et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0249525 A1 | 9/2010 | Shelton, IV et al. |
| 2010/0261970 A1 | 10/2010 | Shelton, IV et al. |
| 2010/0261972 A1 | 10/2010 | Widenhouse et al. |
| 2010/0261974 A1 | 10/2010 | Shelton, IV et al. |
| 2010/0262080 A1 | 10/2010 | Shelton, IV et al. |
| 2010/0268162 A1 | 10/2010 | Shelton, IV et al. |
| 2010/0274093 A1 | 10/2010 | Shelton, IV |
| 2010/0280327 A1 | 11/2010 | Nobis et al. |
| 2010/0312060 A1 | 12/2010 | Widenhouse et al. |
| 2010/0312061 A1 | 12/2010 | Hess et al. |
| 2010/0312062 A1 | 12/2010 | Cropper et al. |
| 2010/0312063 A1 | 12/2010 | Hess et al. |
| 2010/0312064 A1 | 12/2010 | Weisenburgh, II et al. |
| 2010/0312065 A1 | 12/2010 | Shelton, IV et al. |
| 2010/0312066 A1 | 12/2010 | Cropper et al. |
| 2010/0312189 A1 | 12/2010 | Shelton, IV et al. |

FOREIGN PATENT DOCUMENTS

| | | |
|---|---|---|
| EP | 568383 A1 | 11/1993 |
| EP | 577400 A1 | 1/1994 |
| EP | 0637431 A1 | 2/1995 |
| EP | 646358 A1 | 4/1995 |
| EP | 709918 | 5/1996 |
| EP | 0776231 B1 | 6/1997 |
| EP | 950376 | 10/1999 |
| EP | 1219251 A1 | 7/2002 |
| EP | 1219252 A1 | 7/2002 |
| EP | 1219253 A1 | 7/2002 |
| EP | 1350476 | 10/2003 |
| EP | 1702575 A2 | 9/2006 |
| EP | 1731105 A1 | 12/2006 |
| EP | 1774918 A1 | 4/2007 |
| EP | 2119404 A1 | 11/2009 |
| FR | 2710270 A1 | 3/1995 |
| JP | 2006320750 | 11/2006 |
| WO | 9407552 A1 | 4/1994 |
| WO | 9602297 A1 | 2/1996 |
| WO | 9608897 A1 | 3/1996 |
| WO | 9636283 A1 | 11/1996 |
| WO | 9743958 A1 | 11/1997 |
| WO | 0032263 A1 | 6/2000 |
| WO | 0041759 A1 | 7/2000 |
| WO | 0108563 A2 | 2/2001 |
| WO | 0217800 A2 | 3/2002 |
| WO | 2004030515 A2 | 4/2004 |
| WO | 200500454 A1 | 1/2005 |
| WO | 2005002454 A1 | 1/2005 |
| WO | 2005087112 A1 | 9/2005 |
| WO | 2005094432 A2 | 10/2005 |
| WO | 2005097019 A2 | 10/2005 |
| WO | 2005097234 A2 | 10/2005 |
| WO | 2006057982 A2 | 6/2006 |
| WO | 2007008741 A1 | 1/2007 |
| WO | 2007119232 A2 | 10/2007 |
| WO | 2008024502 A2 | 2/2008 |
| WO | 2008028149 A2 | 3/2008 |
| WO | 2008121294 A1 | 10/2008 |
| WO | 2009035663 A2 | 3/2009 |

OTHER PUBLICATIONS

International Search Report, from PCT/US10/36829, mailed Sep. 9, 2010 (5 pages).

European Search Report, EP 10250732, dated Jul. 28, 2010.

International Search Report and Written Opinion for Application No. PCT/US2010/037190, dated Sep. 22, 2010 (15 pages).

"Surgeon performs single-port laparoscopic surgery > Kidney removal with instructions inserted through single port access SPA > One Port Umbilicus Surgery OPUS > Uretero-pelvic junction repair > Bilateral pyeloplasy > Triport > Quadport > R-Port laparoscopic access device > Advanced Surgical Concepts ASC" Ideas for Surgery.com, Dec. 2007, 4 pages.

Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.

Nakajima K, et al. Hand-assisted laparoscopic colorectal surgery using GelPort, Surg Endosc. 2004 Jan; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation, Journal of Endourology," vol. 18, No. 7, Sep. 2004, pp: 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

(56) References Cited

OTHER PUBLICATIONS

International Search Report and Written Opinion for Application No. PCT/US2010/036806, dated Sep. 3, 2010 (8 pages).
International Search Report and Written Opinion for Application No. PCT/US2010/036820, dated Oct. 22, 2010 (18 pages).
U.S. Appl. No. 12/420,107 ("Retractor with Flexible Sleeve" of Shelton et al.).
U.S. Appl. No. 12/420,202 ("Surgical Access Device Having Removable and Replaceable Components" of Shelton et al.).

* cited by examiner

INTERLOCKING SEAL COMPONENTS

FIELD

The present invention relates to methods and devices for accessing a surgical site, and more particularly to methods and devices that allow for the customization of surgical seal elements by an end user.

BACKGROUND

Minimally invasive surgical techniques such as endoscopies and laparoscopies are often preferred over traditional open surgeries because the recovery time, pain, and surgery-related complications are typically less with minimally invasive surgical techniques. In many laparoscopic procedures, the abdominal cavity is insufflated with carbon dioxide gas to a pressure of approximately 15 mm Hg. The abdominal wall is pierced and a cannula or trocar that is approximately 5 to 10 mm in diameter is inserted into the abdominal cavity. Surgeons can then perform a variety of diagnostic procedures, such as visual inspection or removal of a tissue sample for biopsy, or treatment procedures, such as removal of a polyp or tumor or restructuring tissue.

Because of the rise in popularity of minimally invasive surgeries, there has been significant development with respect to the procedures and the instruments used in such procedures. For example, in some procedures a single incision at the navel can be sufficient to provide access to a surgical site. This is because the umbilicus can be a preferred way to access an abdominal cavity in a laparoscopic procedure. The umbilical incision can be easily enlarged without significantly compromising cosmesis and without significantly increasing the chances of wound complications, thus allowing multiple instruments to be introduced through a single incision.

Current devices used in single site laparoscopic procedures are generally prefabricated to include particular configurations. While effective, surgeons typically do not have the ability to customize surgical access devices for a particular use or procedure. It would be desirable to allow a surgeon to easily customize a surgical access device based on the needs of a particular procedure being performed on a particular patient.

Accordingly, there is a need for improved methods and devices that provide end users of surgical access devices the ability to easily customize the devices for a desired use.

SUMMARY

Methods and devices are generally provided that allow a surgeon to easily customize a surgical access device during a surgical procedure. In one embodiment a surgical access device includes a plurality of elongate seal elements that are configured to be placed in a surgical opening to form a seal between a body cavity adjacent to the surgical opening and an outside environment. Each seal element can include one or more mating elements, which can be configured to mate to an adjacent seal element, and a sealable opening. The sealable opening can be configured to receive a surgical instrument while maintaining the seal between the body cavity adjacent to the surgical opening and the outside environment. The sealable opening can also be configured to accommodate movement of the surgical instrument while maintaining the seal between the body cavity adjacent to the surgical opening and the outside environment.

The device can also include one or more tissue coupling elements formed on at least one of the seal elements. The tissue coupling elements can be configured to enable the seal element to coupled directly to tissue that defines the surgical opening. In one embodiment the one or more mating elements of the elongate seal elements include cooperating pliable components that are configured to form a seal therebetween. In another embodiment the one or more mating elements of the elongate seal elements include one or more cooperating rail and guide components that are configured to form a seal therebetween. The rail and guide components can be configured to be snap-fit together. The rail and guide components can also be configured to slide with respect to teach other. In yet another embodiment at least one of the one or more mating elements and the one or more tissue coupling elements can include a plurality of nano-sized voids and nano-sized tubes for forming the seal between the body cavity and the outside environment. Movement in the surgical instrument can include movement in at least one of a plane parallel to the surgical opening and a plane perpendicular to the surgical opening. Optionally, the surgical access device can also include a retractor that is configured to be placed in the surgical opening and to receive the plurality of elongate seal elements. In embodiments that include a retractor, the one or more tissue coupling elements can couple to the retractor and the retractor can be disposed between the seal elements and the tissue of the surgical opening.

One exemplary embodiment of a kit for accessing a surgical site can include a plurality of interchangeable seal elements that are configured to removably and replaceably couple to one another to form a seal assembly for placement into a surgical opening in tissue. The seal assembly can be effective to form a seal between a body cavity adjacent to the surgical opening and an outside environment. Each seal element can include a sealable opening formed therein, and further, each opening can be configured to receive at least one surgical instrument such that the instrument is able to move within the opening while maintaining the seal. Optionally, the kit can include a retractor configured to be placed in the surgical opening and to receive the plurality of elongate seal elements. In one embodiment the seal elements can further include complimentary mating elements that are disposed thereon and that are configured to mate to an adjacent structure. The structure can be at least one of a sea element, a retractor, and tissue. In another embodiment the seal elements can further include a plurality of nano-sized voids and nano-sized tubes for forming a seal between an outside environment and a surgical location.

In one embodiment of a method for accessing a surgical site, at least one seal element can be positioned in an opening in tissue. The seal element can include an elongate sealable opening. At least one surgical instrument can be inserted into the sealable opening of the seal element and manipulated while maintaining a seal between a body cavity adjacent to the opening in tissue and the outside environment. Additional seal elements can also be inserted into the surgical opening. For example, at least one additional seal element can be positioned in the opening in tissue to form a seal between each of the seal element, the additional seal element(s), and the tissue. The additional seal element(s) can also have an elongate sealable opening. At least one surgical instrument can be inserted into the sealable opening of the additional seal element(s). In one embodiment a surgical site can be insufflated through at least one of the openings in the seal elements. Optionally, a retractor can be positioned in the opening in tissue, between the seal element(s) and the tissue, to form a seal between the refractor and the tissue, as well as between the refractor and the seal element(s).

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A surgical access device is generally provided for minimally-invasive surgeries such as laparoscopic surgeries. The surgical access device can be disposed in a body to allow for access to a surgical site from outside of the body. The device can generally be configured to receive one or more instruments through the device so that the instruments can be used to perform a desired procedure. The device can have a number of different components, but in an exemplary embodiment shown in FIG. 1, a surgical device 10 includes a retractor 20 and one or a plurality of seal elements 30, 40, and 50, each configured to be placed in a surgical opening in tissue. Together the retractor 20 and the seal elements 30, 40, 50 form a seal between a surgical location, such as a body cavity adjacent to the surgical opening, and an outside environment.

Figure 1:
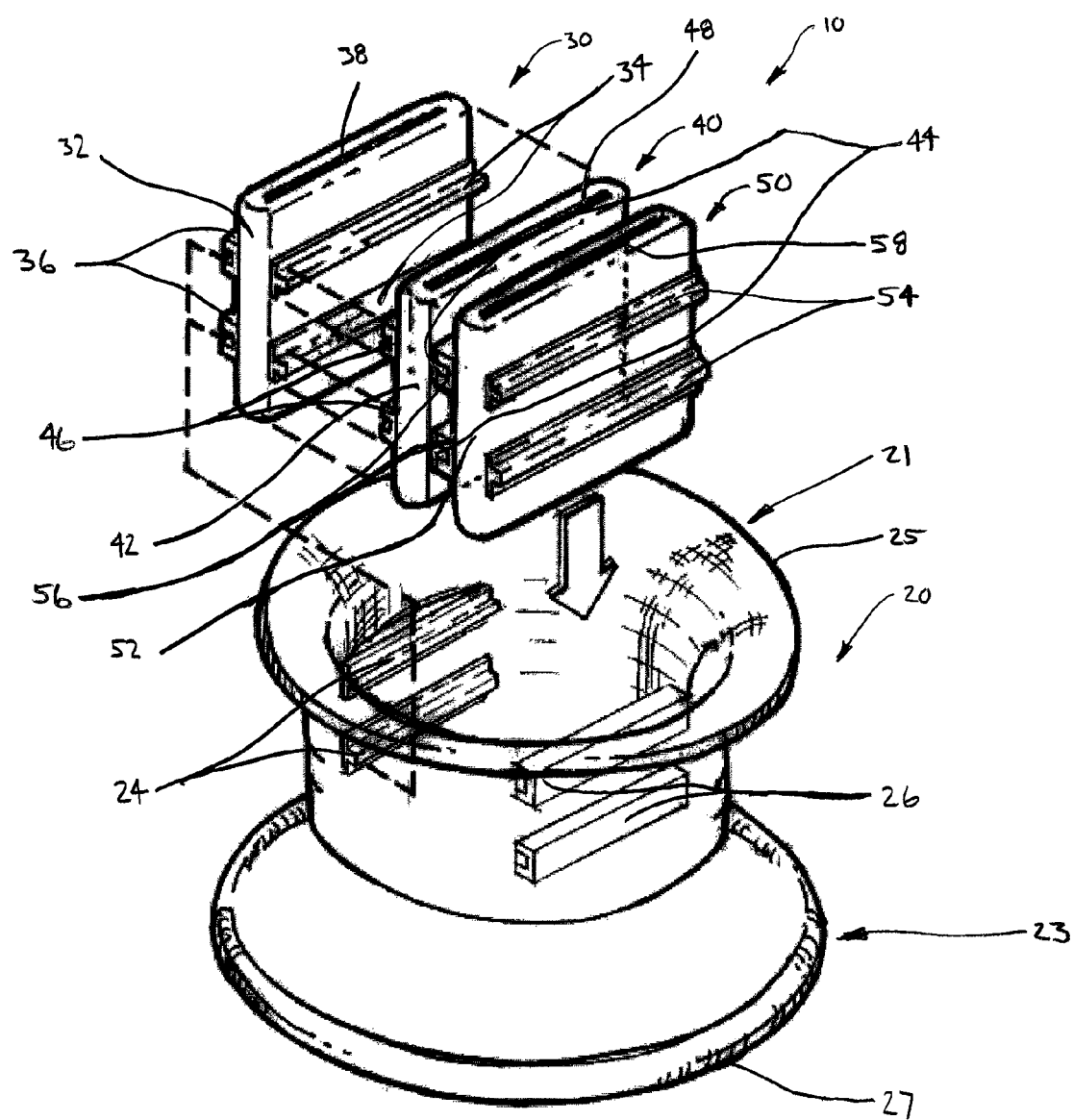
FIG. 1 is an exploded partially transparent perspective view of one exemplary embodiment of a surgical access device.

The seal elements 30, 40, 50 can be configured to couple together to limit or prevent fluid from passing therebetween, and the outermost seal elements, as shown in FIG. 1 the seal elements 30 and 50, can be configured to mate to the retractor 20 to limit or prevent fluid from passing between the seal elements 30, 50 and the retractor 20. Any number of seal elements can be used, but in the illustrated embodiment there are three seal elements 30, 40, and 50. The seal elements 30, 40, 50 can include mating elements or features that are complimentary to each other. In the illustrated embodiment the mating features include rails 34, 44, and 54 and guides 36, 46, and 56 disposed on opposite sides of a body 32, 42, and 52 of the seal elements 30, 40, and 50, respectively. As shown, the rails 34 of the seal element 30 are complimentary to the guides 46 of the seal element 40 and the rails 44 of the seal element 40 are complimentary to the guides 56 of the seal element 50, thus allowing the seal elements 30, 40, and 50 to couple or mate to each other. The guides 36 of the seal element 30 and the rails 54 of the seal element 50 on an outer side of the bodies 32 and 52, respectively, can be complimentary to rails 24 and guides 26 of the retractor 20, thus allowing these components to couple or mate together as well. Each seal element 30, 40, 50 can also include an opening 38, 48, 58, respectively, to allow an instrument to pass through for use at a surgical site, such as a body cavity. It can be advantageous that the seal elements 30, 40, and 50 cooperate in a manner that allows each seal element to be removable and replaceable with respect to the other seal elements. Further, it can also be advantageous that the seal elements 30, 40, and 50 be configured to be interchangeable such that seal elements can be substituted in or out of one configuration to create another desired configuration.

Each of the components of the surgical access device 10 can have a variety of configurations. The refractor 20, for example, can be generally configured to be disposed within an incision formed through tissue to form a working channel extending into a body cavity. The retractor 20 can form a seal between tissue in which it is disposed and the retractor 20 itself. While the retractor 20 can have a variety of shapes, depending at least in part on the size of the incision in which it will be disposed, the surgical device components with which it will be used, and the type of surgical procedure with which it will be used, in one exemplary embodiment the retractor 20 is an elongate hollow cylindrical member having a proximal portion 21 and a distal portion 23 configured to retract tissue away from an incision in which it is disposed. Although the illustrated embodiments include retractors having features for retracting tissue on both sides of a surgical opening, in alternative embodiments the retractor 20 can be configured to couple to other devices. For example, the retractor 20 can be configured to be only partially disposed in an incision and can then be configured to couple to another component that extends through the remainder of the opening. Some exemplary embodiments of retractors that can be configured to couple to other components of a surgical access device are described in greater detail in U.S. patent application Ser. No. 12/420,202 entitled "Surgical Access Device Having Removable and Replaceable Components" of Shelton et al., and filed on Apr. 8, 2009, which is hereby incorporated by reference in its entirety.

The retractor 20 can be configured to be generally flexible, and thus can be made from a flexible material, such as a polymer. Examples of flexible materials that can be used to form the retractor 20 include polyisoprene, polyurthethane, and silicone. More than one material can be used for form the retractor 20, and the retractor 20 can include portions that are more rigid than other portions. For example, more rigid portions of a retractor can be made from materials such as polycarbonate, polyester, polyetherimide material, or stainless steel, while more flexible portions can be made from materials such as polyisoprene, polyurthethane, and silicone. Another non-limiting exemplary embodiment of a retractor that can be used with the teachings described herein is described in greater detail in U.S. patent application Ser. No. 12/420,107 entitled "Retractor with Flexible Sleeve" of Shelton et al., and filed on Apr. 8, 2009, which is hereby incorporated by reference in its entirety.

Just as the retractor 20 can have a variety of shapes, it can also have a variety of sizes. The size of the retractor 20 can depend at least on the some of the same factors that affect the shape of the retractor, including the size of the incision in which it will be disposed, surgical devices components with which it will be used, and the type of surgical procedure with which it will be used. In the illustrated embodiment the retractor 20 is configured such that both the proximal and distal portions 21 and 23 include rings 25 and 27, respectively, to assist with retracting tissue away from a surgical opening. As shown, ring 27 of the distal portion 23 has a larger diameter than the ring 25 of the proximal portion 21, but in alternative embodiments the rings 25 and 27 can have approximately similar diameters or the ring 25 of the proximal portion 21 can be larger than the ring 27 of the distal portion 23. In addition to assisting with tissue retraction, the rings 25 and 27 can provide stability to assist with holding the surgical access device 10 in an incision in which it is disposed. The rings 25 and 27 can be formed integrally with or be disposed within flanges of the proximal and/or distal portions 21 and/or 23. In an exemplary embodiment the diameters of the proximal and distal portions 21 and 23 of the retractor 20 can be approximately in the range of 0.5 to 5 cm. In one exemplary embodiment a maximum diameter of the flange of the distal portion 23 is approximately twice as large as a diameter of the flange of the proximal portion 21. The size of any portion of the retractor 20, or any other portion of the surgical device 10 for that matter, can be adjusted based at least on the intended use of the device 10.

Disposed in the retractor 20 can be one or a plurality of seal elements 30, 40, 50. The seal elements 30, 40, and 50 can have bodies 32, 42, and 52 and can be generally configured to both receive instruments through a sealable opening 38, 48, and 58 for use at a surgical site and to maintain a seal between a surgical site and an outside environment, thereby limiting or preventing fluid from passing therebetween. The seal elements 30, 40, 50 can maintain the seal within the seal elements 30, 40, 50 via the sealable openings 38, 48, 58, between respective seal elements via cooperative mating elements or features, and between the outermost seal elements 30, 50 and the retractor 20. For example, with respect to the seal formed by the sealable openings 38, 48, 58, the sealable openings 38, 48, 58 can be configured to conform and seal around an instrument disposed therein. When no instrument is disposed in the sealable opening 38, 48, 58, it can be configured to seal itself. Examples of a variety of configurations that can be used to form a seal between respective seal elements, seal elements and a retractor, and seal elements and tissue are discussed in greater detail below.

While the sealable openings 38, 48, 58 can be configured to conform and seal around a surgical instrument, they can also be configured to allow for movement of an instrument disposed therein while still maintaining the seal. Movement of an instrument can occur in any direction with respect to the sealable openings 38, 48, 58, and in more than one direction at a time, while still maintaining a seal between a surgical site and an outside environment. For example, the sealable openings 38, 48, 58 can be configured to allow for an instrument to move in a plane that is parallel to a surgical opening. The sealable openings 38, 48, 58 can also be configured to allow for an instrument to move in a plane that is perpendicular to a surgical opening. Other examples of directional movement include, but are not limited to, an angular direction and a vertical direction. Even as movement of an instrument occurs in the sealable openings 38, 48, 58, the sealable openings 38, 48, 58 can continue to maintain the seal between a surgical site, such as a body cavity adjacent to the surgical opening in which the seal elements 30, 40, 50 are disposed, and an outside environment.

The shape, size, number, and purpose of the seal elements 30, 40, and 50 can vary, depending at least in part on the size of the incision and/or retractor in which they will be disposed, the surgical device components and instruments with which they will be used, and the type of surgical procedure with which they will be used. In the illustrated embodiment the seal elements 30, 40, and 50 are generally elongate and rectangular. A slit in each of the seal elements 30, 40, and 50 forms the sealable openings 38, 48, and 58, respectively. While in the illustrated embodiment each of the seal elements 30, 40, 50 is approximately the same size and shape, in alternative embodiments one or more of the seal elements can have a different size and/or shape than the other seal elements. While the size of the seal elements 30, 40, 50 can vary, and can depend at least in part on the size of the surgical opening and/or retractor in which they are disposed, in one exemplary embodiment they have a length approximately in the range of 1.5 to 3.5 centimeters, a height approximately in the range of 2 to 7 centimeters, and a thickness approximately in the range of 6 to 12 millimeters.

Seal elements of different sizes and shapes can be mixed and matched to allow a surgeon to configure a desired set-up for use with a particular surgical procedure on a particular patient. For example, elongate seal elements having varying thicknesses can be used, or alternatively, one or more other types of seal elements can be used with elongate seal elements or with other types of seal elements. Other types of seal elements that can be used include gel, multi-layer, duckbill, gimbal, zero-closure, diaphragm, and septum seal elements, each of which can serve particular purposes. The seal elements 30, 40, 50 used in the surgical access device 10, regardless of the number, size, shape, or purpose, can generally be removable, replaceable, and interchangeable.

The seal elements 30, 40, 50 can also be made of a variety of materials, but generally can be configured to be flexible. Flexibility of the seal elements 30, 40, 50 can assist the seal elements 30, 40, 50 in allowing the instrument to make desired movements while still maintaining the desired seal. In one embodiment the seal elements 30, 40, 50 can be made of a polymer. Examples of flexible materials that can be used to form the bodies 32, 42, 52 of the seal elements 30, 40, 50 include polyisoprene, polyurthethane, and silicone. Although flexible, the seal elements 30, 40, 50 can also have some rigidity to help protect any instruments disposed therein and to maintain a general location of the seal elements 30, 40, 50 within the surgical opening and/or the refractor 20.

The seal elements 30, 40, 50 can also include one or more mating elements or features. A variety of different mechanisms can be used to form the mating elements, some of which are discussed in greater detail herein. The mating features can be used to form a seal between two elements, such as between two seal elements, between a seal element and a retractor, and/or between a seal element and tissue of a surgical opening. The mating features aid in making the seal elements 30, 40, 50 removable, replaceable, and interchangeable.

Figure 2A:
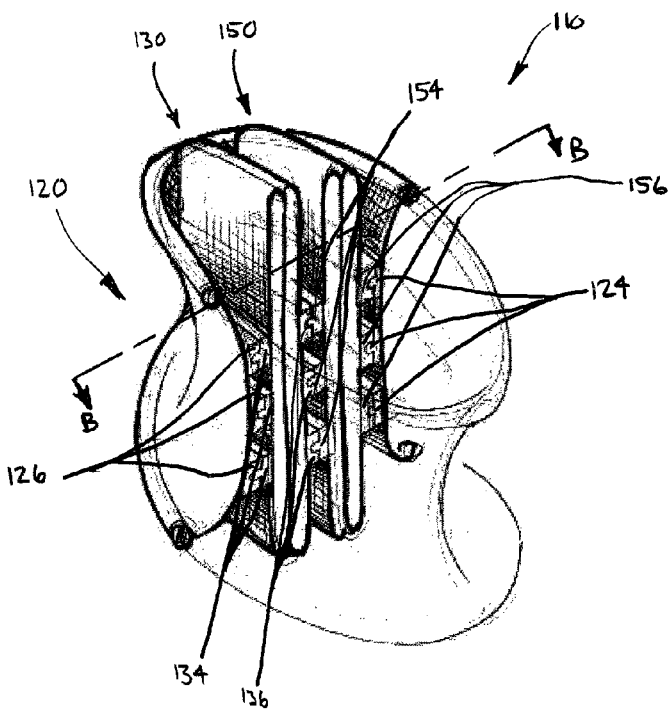
FIG. 2A is a partially transparent cross-sectional view of another exemplary embodiment of a surgical access device.
Figure 2B:
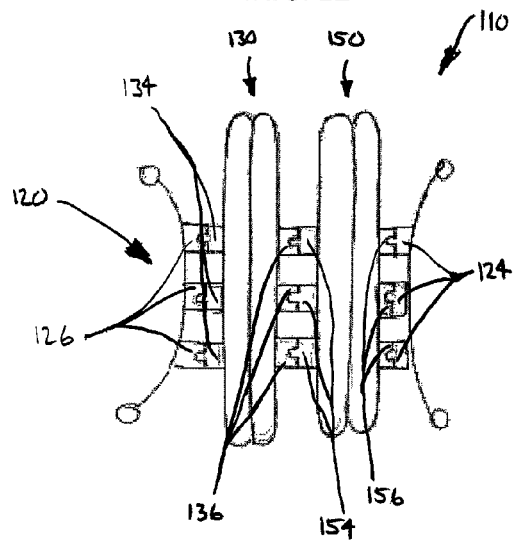
FIG. 2B is a side cross-sectional view of the surgical access device of FIG. 2A taken at line B-B.
Figure 2C:
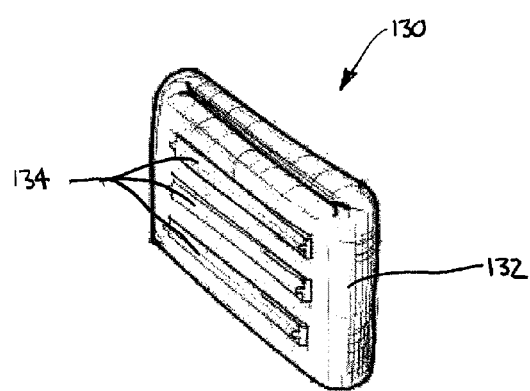
FIG. 2C is a perspective view of one elongate seal element of the surgical access device of FIG. 2A.

In the one embodiment shown in FIGS. 1-2C, the mating features of the seal elements 30, 40 and 50 include a pair of complimentary rails 34, 44, and 54 and guides 36, 46, and 56, respectively. The seal elements 30, 40, 50 can include a pair of rails 34, 44, 54 on one side of the body 32, 42, 52 and a pair of guides 36, 46, 56 on the other side of the body 32, 42, 52. As illustrated, the rails 34 of the seal element 30 are configured to mate with guides 46 of the adjacent seal element 40 to form a seal therebetween and the rails 44 of the seal element 40 are configured to mate with guides 56 of the adjacent seal element 50 to also form a seal therebetween. The guides 36 of the seal element 30 and rails 54 of the seal element 50 formed on outer bodies 32 and 52 of the outermost seal elements 30 and 50, respectively, can be configured to mate with complimentary rails 24 and guides 26 of the retractor 20. The rails 24, 34, 44, 54 and guides 26, 36, 46, 56 can be configured to mate in a number of different manners, for instance by being snap-fit, by being slidingly engaged, and/or by way of an interference fit. Rails 24, 34, 44, 54 and guides 26, 36, 46, 56 can be formed from a variety of materials, such as, for example, stainless steel.

The rails 34, 44, and guides 46, 56 can be coupled or mated together prior to inserting the seal elements 30, 40, and 50 into the retractor 20, or alternatively, they can be coupled or mated together as or after they are inserted into the surgical opening and/or the retractor 20. Any number of seal elements and mating elements can be used. For example, as illustrated in FIGS. 2A-2B of a surgical access device 110, only two seal elements 130, 150 are used and each seal element 130, 150 can include three complimentary rails 134, 154 and guides 136, 156, respectively. As shown, the two seal elements 130, 150 are disposed in a housing 120 that can be inserted into a surgical opening for accessing a surgical site. The housing 120 of the illustrated embodiment can be configured in a similar manner as the retractor 20 of the surgical access device 10 of FIG. 1, and thus can be configured to form a seal between a surgical site and an outside environment, and further, can be configured to receive the seal elements 130, 150 by way of rails 124 and guides 126 located on an inner surface thereof. The housing 120 can also be configured to retract tissue of the surgical opening. In the illustrated embodiment the complimentary rails 124, 134, 154 and guides 126, 136, 156 are configured to allow sliding movement of the seal elements 130, 150 with respect to each other and with respect to the housing 120. Sliding movement can provide additional flexibility in a surgical procedure. As shown in FIG. 2C, the rails 134 and guides (not visible) can be configured in a substantially horizontal direction with respect to a body 132 of the seal element 130, although in other embodiments the rails 134 and guides can be placed at an angle with respect to the body 132, or even in a vertical direction with respect to the body 132 of the seal element 130.

Figure 3:
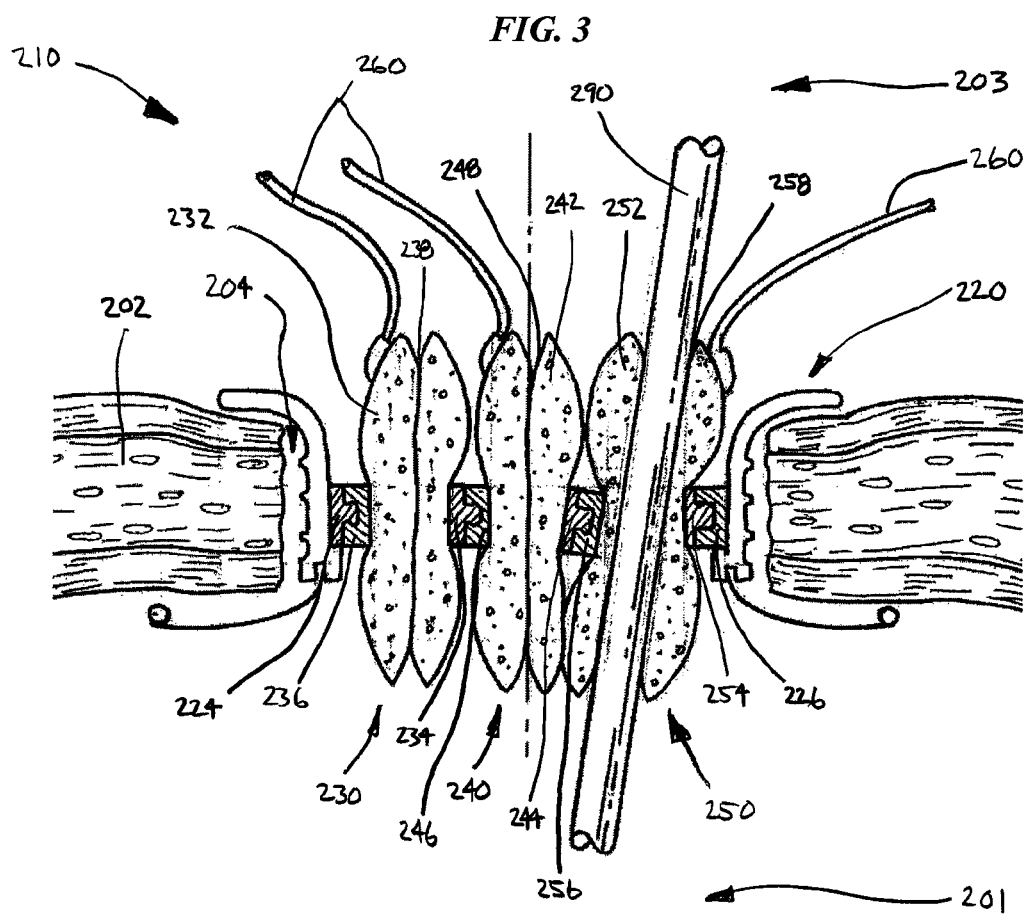
FIG. 3 is a side view of another exemplary embodiment of a surgical access device that is disposed in tissue.

In another embodiment of a surgical access device 210, illustrated by FIG. 3, each of the seal elements 230, 240, and 250 can include only a single mating element. As shown, a retractor 220 is disposed in an opening 204 in tissue 202 and three seal elements 230, 240, 250 are connected together to form a seal between a surgical site 201 and an outside environment 203. Each of the seal elements 230, 240, 250 can include a single rail 234, 244, 254 and a single guide 236, 246, 256, respectively, located on a body 232, 242, 252 of the seal elements 230, 240, 250 and that can be complimentary to adjacent guides and rails of the seal elements 230, 240, 250 and the retractor 220. A surgical instrument, such as tool 290, can be disposed in a sealable opening 238, 248, 258 of at least one of the seal elements 230, 240, 250, and as shown, the sealable opening 258 can conform around the instrument 290 to limit or prevent fluid from passing between the surgical site 201 and the outside environment 203.

While the retractor 220 and/or seal elements 230, 240, and 250 can be configured to provide a number of different configurations by substituting seal elements into and out of the device 210, additional adaptability of the device 210 can be provided by adjustment mechanisms located adjacent to or coupled to the seal elements 230, 240, 250. In the embodiment shown in FIG. 3, a seal control mechanism 260 is connected to each of the seal elements 230, 240, 250 and is configured to insufflate or remove fluid, such as air, from the bodies 232, 242, 252 of the seal elements 230, 240, 250. The seal elements 230, 240, 250 can be expanded and contracted into a number of different configurations during a surgical procedure based on the amount of fluid supplied to each seal element 230, 240, 250, thus creating additional customization options for the end user. Further discussion of the seal control mechanisms 260, as well as other adjustment mechanisms that can be used in conjunction with the disclosed systems, devices, and methods, are described in greater detail in U.S. application Ser. No. 12/479,092 entitled "Active Seal Components" of Shelton et al. and filed concurrently with the present application, which is hereby incorporated by reference in its entirety.

Figure 4A:
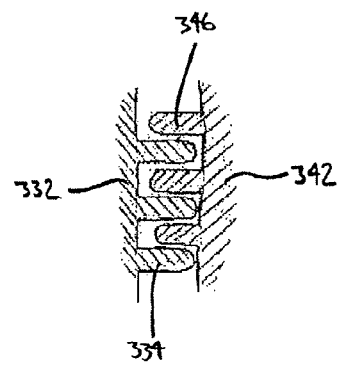
FIG. 4A is a schematic view of one embodiment of mating features for use with elongate seal elements of a surgical access device.
Figure 4B:
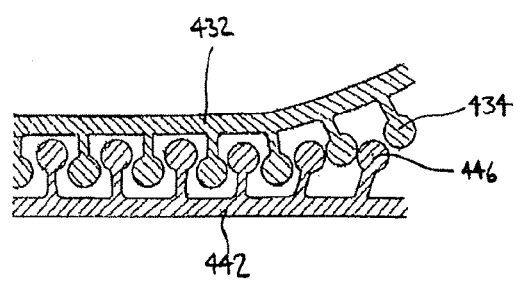
FIG. 4B is a schematic view of another embodiment of mating features for use with elongate seal elements of a surgical access device.

FIGS. 4A-4E illustrate a variety of other mating elements or features that can be used to provide a seal between adjacent seal elements, seal elements and a retractor, and/or seal elements and tissue. For example, in FIG. 4A a plurality of small, pliable, rigid, and straight pillars are illustrated that mate together to form a seal. A first set of straight pillars 334 can be disposed on a side of a body 332 of a sealing element and a second, complimentary set of straight pillars 346 can be disposed on a side of a body 342 of a second sealing element. The two sets of pillars 334, 346 can be brought into contact, thereby allowing a seal to be formed therebetween. The pillars can be any shape, including circular, as illustrated by FIG. 4B. As shown, a first set of rounded pillars 434 can be disposed on a side of a body 432 of a sealing element and a second, complimentary set of round pillars 446 can be disposed on a side of a body 442 of a second sealing element. The two sets of pillars 434, 446 can be brought into contact, thereby allowing a seal to be formed therebetween.

Figure 4C:
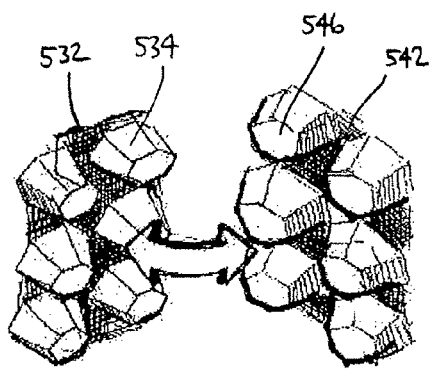
FIG. 4C is a perspective view of yet another embodiment of mating features for use with elongate seal elements of a surgical access device.
Figure 4D:
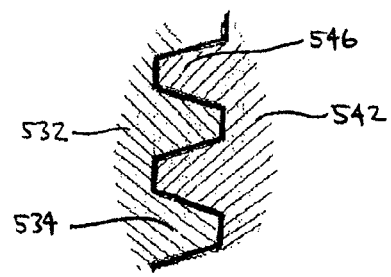
FIG. 4D is a schematic view of the mating features of FIG. 4C.

Another example of a shape that can be used to form a seal is illustrated in FIGS. 4C and 4D. In this embodiment a first set of hexagonal pillars 534 are disposed on a side of a body 532 of a sealing element 530 and a second, complimentary set of hexagonal pillars 546 are disposed on a side of a body 542 of a second sealing element. The two sides can be brought together, as shown in FIG. 4C, and engage each other to form a seal, as shown in FIG. 4D. A person skilled in the art will recognize that a variety of other shapes can also be used to form a seal between two elements. In fact, any combination of shapes, sizes, and materials can be used, although in an exemplary embodiment each of the pillars has a length approximately in the range of 1 to 4 millimeters, a width that can be the same as a thickness or can be continuous across the entire body in the range of approximately 1.5 to 3.5 centimeters, and a thickness approximately in the range of 0.5 to 1 millimeter and are made of polypropylene, polyethylene, isoprene, sanoprene, polyurethane, and/or silicone. The same material that is used to form the seal element can also be used to form the pillars. Further, although the discussed embodiments make reference to mating two seal elements, the complimentary pliable components can likewise be located on a retractor for attachment of a seal element thereto or on tissue so that a seal element can be attached to tissue without the need of a retractor.

Figure 4E:
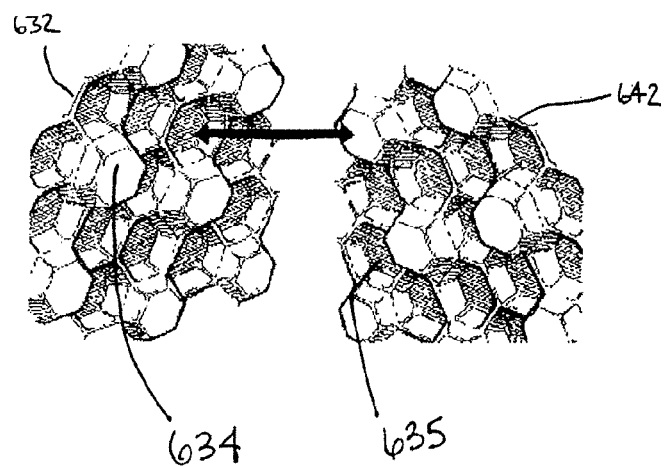
FIG. 4E is a perspective view of still another embodiment of mating features for use with elongate seal elements of a surgical access device.

FIG. 4E illustrates yet another embodiment of a coupling or mating feature. As shown, each of two seal elements can include bodies 632 and 642 having a plurality of nano-sized voids 634 and/or nano-sized tubes 635. While the voids 634 and/or tubes 635 can be complimentary, similar to the pillars 334, 346, 434, 446, 534, 546 discussed with respect to FIGS. 4A-4D, they do not have to be. Rather, the voids 634 and/or tubes 635 can be of a nature such that just be engaging other voids, defects, tubes and/or protrusions a seal can be formed therebetween. A diameter of the voids, defects, tubes, and/or protrusions can be in the range of approximately 0.5 to 1 millimeter and can have a height or depth in the range of approximately 1 to 4 millimeters. Any number and consistency of voids, defects, tubes, and/or protrusions can be used to form the seal. Because of the number of voids 634 and/or tubes 635 disposed on the surface of the bodies 632, 642, they engage each other to create an adhesive force. The seal forms much in the same manner as a seal can be formed by the feet of a gecko between its feet and a surface. The voids 634 and/or tubes 635 are able to grip each other and create a seal therebetween. The seal can be formed in both wet and dry environments, and thus the seal can be maintained throughout a surgical procedure. Alternatively, or additionally, a plurality of nano-fibers can be used to form a similar adhesive effect. Because the mating features of FIG. 4E do not need complimentary mating features on an adjacent seal element, retractor, or tissue, the nano-sized voids 634 and/or nano-sized tubes 635 can be particularly advantageous for mating directly to tissue. The nano-sized voids 634 and/or nano-sized tubes 635 can engage nano-sized voids, defects, and/or protrusions of the tissue and form a seal therebetween without having to attach any component or structure to the tissue.

Figure 5:
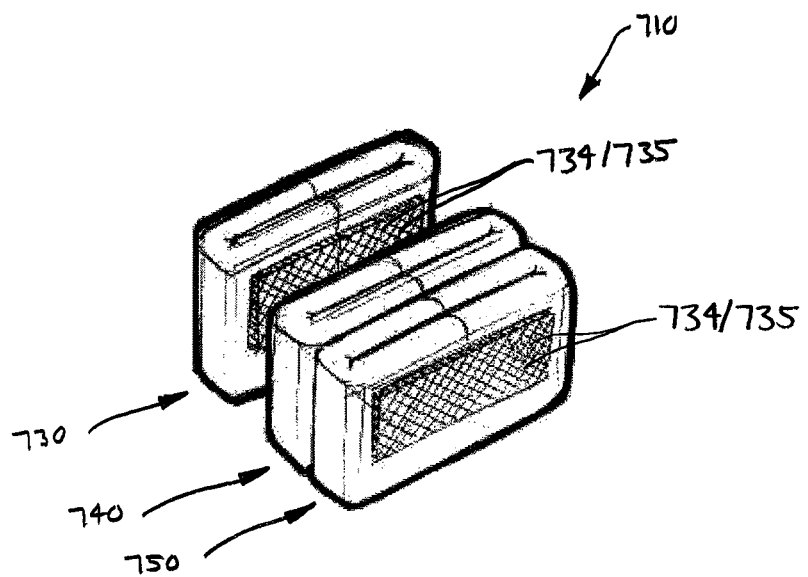
FIG. 5 is a perspective view of one exemplary embodiment of a plurality of elongate seal elements forming a surgical access device.

Because the seal elements can be attached directly to tissue, the seal elements can form a surgical access device and be used in a surgical procedure without the need for a retractor. That is, the seal elements can open and maintain a surgical opening, form a working channel, attach to tissue, and form a sealable opening for one or more instruments. As shown in FIG. 5, a surgical device 710 can be formed from a plurality of seal elements 730, 740, and 750, each including nano-sized voids 734 and/or nano-sized tubes 735 for forming a seal between the seal elements 730, 740, 750 themselves, and to allow the seal elements 730, 740, 750 to form a seal between the outermost seal elements 730 and 750 and tissue in which the seal elements 730, 740, 750 are disposed.

Figure 6A:
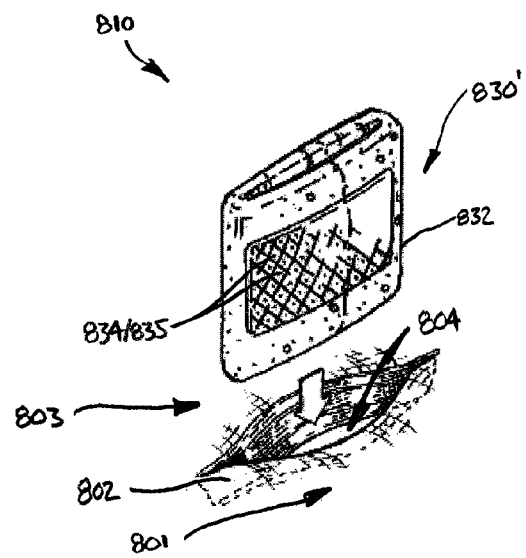
FIG. 6A is a perspective view of one exemplary embodiment of an elongate seal element forming a surgical access device and configured to be disposed in tissue.
Figure 6B:
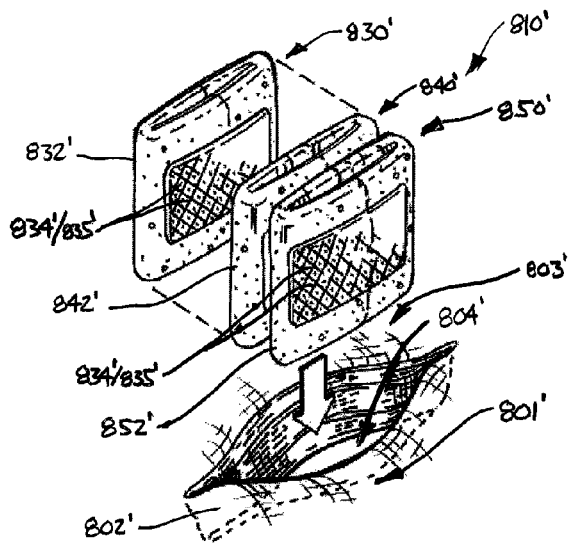
FIG. 6B is a perspective view of another exemplary embodiment of a plurality of elongate seal elements forming a surgical access device configured to be disposed in tissue.

FIG. 6A illustrates an embodiment of a surgical access device 810 in which a seal element 830 having nano-sized voids 834 and/or nano-sized tubes 835 on each side of its body 832 is disposed in a surgical opening 804 formed in tissue 802. The nano-sized voids 834 and/or nano-sized tubes 835 can engage the tissue such that the seal element 830 is in direct contact with tissue. Likewise, FIG. 6B illustrates an embodiment of a surgical access device 810' in which a plurality of seal elements 830', 840', and 850' having nano-sized voids 834' and/or nano-sized tubes 835' on each side of their respective bodies 832', 842', 852' are disposed in a surgical opening 804' formed in tissue 802'. In FIG. 6A each side of the body 832 is the outermost side of the body 832, and thus the nano-sized voids 834 and/or nano-sized tubes 835' serve as tissue mating elements by mating directly to tissue 802. In FIG. 6B the nano-sized voids 834' and/or nano-sized tubes 835' on outer sides of outer bodies 832', 852' of the outermost seal elements 830', 850' can form a seal between the outermost seal elements 830', 850' and the tissue 802'. The remaining nano-sized voids 834' and/or nano-sized tubes 835' can engage adjacent nano-sized voids 834' and/or nano-sized tubes 835' of adjacent seal elements 830', 840', 850' to form a seal therebetween. In both FIGS. 6A and 6B the mating features of the seal elements 830, 830', 840', 850' and the tissue 802, 802' cooperate together to form a seal between a surgical site 801, 801' and an outside environment 803, 803', respectively. Although in the illustrated embodiments the mating feature relied upon includes nano-sized voids 834, 834' and/or nano-sized tubes 835, 835', any mating feature, including others disclosed herein, can also be used in a similar fashion.

Figure 6C:
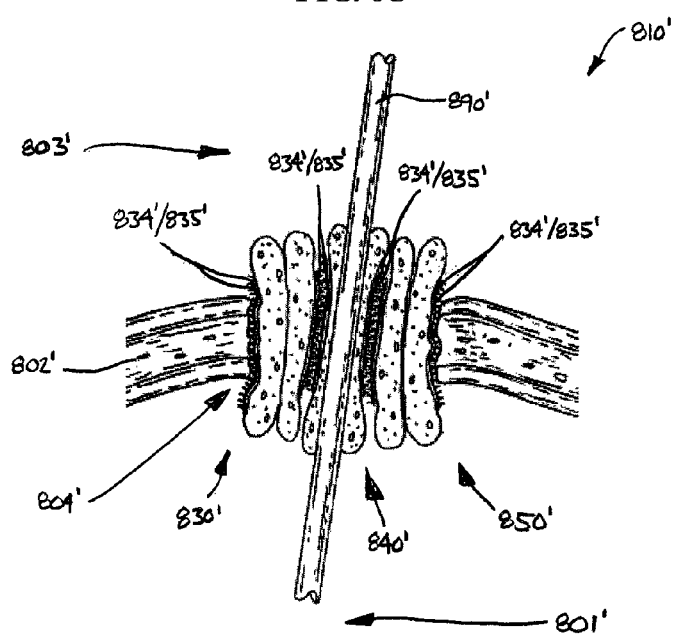
FIG. 6C is a side view of the surgical access device of FIG. 6B disposed in tissue.

FIG. 6C illustrates the seal elements 830', 840', and 850' of the surgical access device 810' of FIG. 6B disposed in the tissue 802' with a surgical instrument 890' disposed in one of the seal elements 840'. As shown, the nano-sized voids 834' and/or nano-sized tubes 835' of the bodies 832' and 852' of the outermost seal elements 830' and 850' couple or mate directly with the tissue 802' of the opening 804' in which the seal elements 830', 840', 850' are disposed. The nano-sized voids 834' and/or nano-sized tubes 835' that are not coupled to the tissue 802' can couple or mate with adjacent nano-sized voids 834' and/or nano-sized tubes 835' of adjacent seal elements 830', 840', 850'. The seal element 840' in which the instrument 890' is disposed can form a seal around the instrument 890' to prevent or limit fluid from traveling between the surgical site 801' and the outside environment 803'.

Figure 7A:
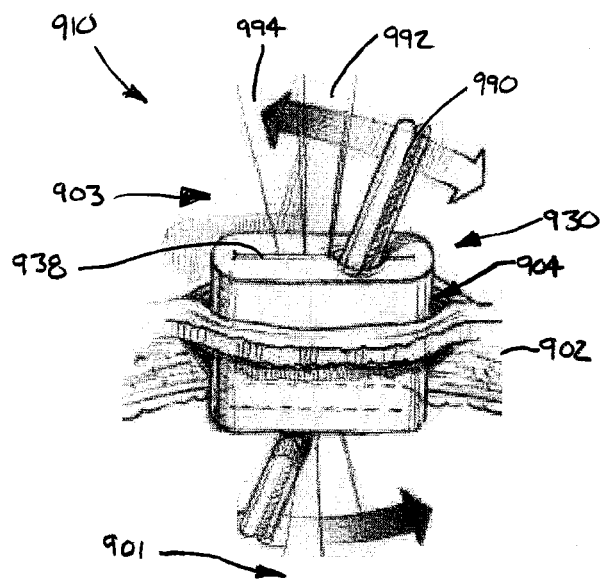
FIG. 7A is a perspective view of another exemplary embodiment of an elongate seal element forming a surgical access device that is disposed in tissue.
Figure 7B:
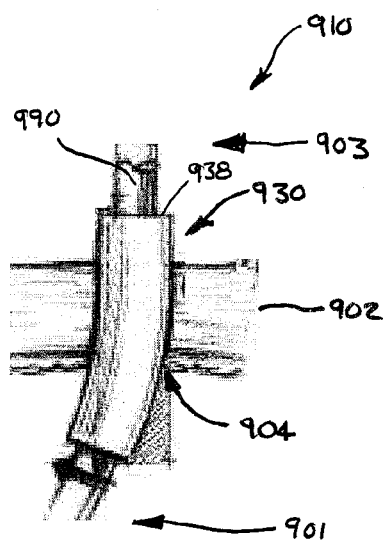
FIG. 7B is a side view of the elongate seal element of FIG. 7A.
Figure 7C:
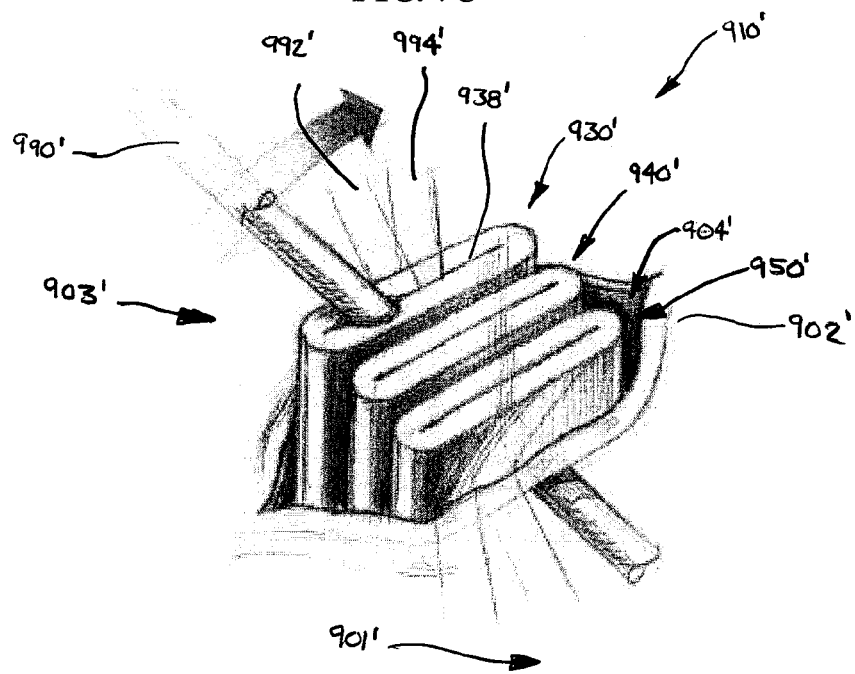
FIG. 7C is a perspective view of yet another exemplary embodiment of a plurality of elongate seal elements forming a surgical access device that is disposed in tissue.

FIGS. 7A-7C illustrate further embodiments of surgical access devices having seal elements disposed directly in tissue, such as an abdominal wall, without the use of a retractor. In FIG. 7A a surgical access device 910 includes a single seal element 930 that can be disposed in an opening 904 in tissue 902 to form a seal between a surgical site 901 and an outside environment 903. One or more surgical instruments can be disposed in a sealable opening 938 of the seal element 930. As shown, three instruments 990, 992, and 994 are disposed in the seal element 930. Each of the instruments 990, 992, 994 can be moved in a variety of directions as desired, including but not limited to angularly and vertically, while a seal formed around each of the instruments 990, 992, 994 by the sealable opening 938 is maintained. FIG. 7B illustrates the flexible nature of the seal element 930. While the seal element 930 generally remains in the opening 904 to maintain the seal between the surgical site 901 and the outside environment 903, it can be allowed to flex during the surgical procedure. Flexing of the seal element 930 does not typically affect its ability to maintain a seal.

FIG. 7C illustrates a surgical access device 910' that includes seal elements 930', 940', and 950', each of which can include more than one instrument disposed therein while maintaining a seal between a surgical site 901' and an outside environment 903'. As shown, three seal elements 930', 940', 950' are disposed in a surgical opening 904' in tissue 902'.

Three instruments 990', 992', and 994' are disposed in the seal element 930', and each of the instruments 990', 992', 994' can be moved in a variety of directions as desired while still maintaining a seal formed by sealable opening 938' of the seal element 930' around each of the instruments 990', 992', 994'. A person skilled in the art will recognize that any number of instruments can be used in a seal element, and further, that any number of seal elements can be used in a surgical opening.

Because of the removable, replaceable, and interchangeable nature of the seal elements, the seal elements can be used to create a surgical kit. A kit can allow for easy customization by a surgeon on site. The kit can include a plurality of seal elements that can be used to form a variety of configurations in a surgical opening. The seal elements can have different sizes, shapes, and purposes, and can be substituted in and out of any number of configurations as desired by a surgeon. The kit can also include a number of different surgical instruments for use with the seal elements, and optionally, can include a retractor. A number of different mating features, both for mating between seal elements and to tissue, can also be included. The mating features can also be removable, replaceable, and interchangeable to allow for even further customization by the end user.

In use, the surgical access device can enable a surgeon to easily customize the device for any number of desired procedures. For convenience, when discussing various methods of using surgical access devices, rather than reciting each of the various embodiments of surgical access devices and their related components, reference will be made to the surgical access devices 710, 710', and their respective components, of FIGS. 6A-6C.

An incision or opening 704 can be formed in a tissue 702 of a body. For example, an incision can be formed in an abdominal wall. A seal element 730 can be positioned in the opening 704 to form a seal directly between the seal element 730 and the tissue 702. The seal element 730 can also form a seal between a surgical site 701 and an outside environment 703. The seal formed between the seal element 730 and tissue 702 can be formed using coupling or mating features, such as, by way of non-limiting example, nano-sized voids 734 and/or nano-sized tubes 735 located on each side of a body 732 of the seal element 730. A seal can also be formed inside the seal element 630 by way of a sealable opening 738.

The seal element 730 can be placed in the opening 704 so that a desired configuration can be achieved. Once the seal element 730 has been positioned in the desired location, an instrument can be inserted in the sealable opening 738 of the seal element 730 to allow the instrument to access the surgical site 701. The seal element 730 can be configured to seal directly around the instrument to limit or prevent fluid from passing between the surgical site 701 and the outside environment 703. The instrument can be manipulated and used as desired. Because there is no housing or retractor used in conjunction with the seal element 730, the instrument moves only within the seal and thus is not constrained by additional components. Further, because the seal element 730 does not move within a housing when an instrument is manipulated therein, additional freedom of movement is provided. Alternatively, more than one instrument can be disposed in the seal element 730 for use at the surgical site 701. Any number of surgical procedures can be performed, and to the extent that items need to be removed from the surgical site 701, such as certain types of tissue specimens, tumors, or other objects or specimens located at the surgical site 701, such items can be removed without losing the seal. The instruments can likewise be removed from the surgical site with the seal element 730 providing the desired sealing effect as and after the instruments are removed.

In other embodiments, as shown in FIGS. 6B and 6C, more than one seal element 730', 740', and 750' can be used. When more than one seal element is used, the outer side of the outer bodies 732' and 752' of the outermost seal elements 730' and 750', respectively, can couple or mate with tissue 702' of a surgical opening 704' to form a seal therebetween, and the portions of the bodies 732', 742', 752' of the seal elements 730', 740', 750' can couple or mate with adjacent bodies 732', 742', 752' of the seal elements 730', 740', 750' to form a seal therebetween. The seal elements 730', 740', 750' can mate in a variety of manners, as discussed at least in more detail above, but generally the seal elements 730', 740', 750' can be disposed in tissue 702' in a configuration desired by the surgeon. For example, in one configuration the surgeon may desire three seal elements each having substantially similar individual configurations. Alternatively, the surgeon may desire four seal elements, each having a different size, shape, and purpose.

In one embodiment a surgeon can use at least one of the seal elements 730', 740', 750' to provide insufflation to the surgical site 701'. Still further, although not illustrated in the embodiment of FIGS. 6B and 6C, a surgeon may desire to include a retractor, for example to assist in retracting tissue away from the surgical opening 704' and/or to provide additional stability for the opening 704'. In an embodiment in which a retractor is used, the outermost seal elements 730' and 750' are not coupled or mated directly to tissue 702', but rather, they are mated to the retractor to form a seal. The retractor provides a seal between the tissue 702' and the retractor as well.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
   a plurality of flexible elongate seal elements configured to be placed in a surgical opening to form a seal between a body cavity adjacent to the surgical opening and an outside environment, each seal element having:
      two sidewalls that are elongate and approximately parallel to each other;
      one or more mating elements disposed on an outer surface of each of the sidewalls and configured to mate directly to at least one of one or more adjacent, separate mating elements of an adjacent seal element, one or more adjacent mating elements of a retractor, and tissue; and
      a sealable opening configured to receive a surgical instrument while maintaining the seal between the body cavity adjacent to the surgical opening and the outside environment, the sealable opening being configured to accommodate movement of the surgical instrument while maintaining the seal between the body cavity adjacent to the surgical opening and the outside environment.

2. The surgical access device of claim 1, wherein the one or more mating elements further comprise cooperating pliable components configured to form a seal therebetween.

3. The surgical access device of claim 1, wherein the one or more mating elements further comprise cooperating rail and guide components configured to form a seal therebetween.

4. The surgical access device of claim 3, wherein the rail and guide components are configured to be snap-fit together.

5. The surgical access device of claim 3, wherein the rail and guide components are configured to slide with respect to each other.

6. The surgical access device of claim 1, wherein at least one of the one or more mating elements further comprise a plurality of voids and tubes for forming the seal between the body cavity and the outside environment.

7. The surgical access device of claim 1, wherein movement of the surgical instrument can include movement in at least one of a plane parallel to the surgical opening and a plane perpendicular to the surgical opening.

8. The surgical access device of claim 1, further comprising a retractor configured to be placed in the surgical opening and to receive the plurality of elongate seal elements.

9. A kit for accessing a surgical site, comprising:
   a plurality of flexible, interchangeable seal elements configured to removably and replaceably couple to one another to form a seal assembly able to be placed into a surgical opening in tissue, the seal assembly being effective to form a seal between a body cavity adjacent to the surgical opening and an outside environment, each seal element having two sidewalls that are elongate and approximately parallel to each other, a sealable opening formed therein, and each opening being configured to receive at least one surgical instrument such that the at least one surgical instrument is able to move within the opening while maintaining the seal,
   wherein each of the plurality of interchangeable seal elements further comprises one or more mating elements disposed on an each of at least one of the sidewalls and configured to mate directly to at least one of one or more adjacent mating elements of a seal element, one or more adjacent mating elements of a retractor, and tissue.

10. The kit of claim 9, further comprising a retractor configured to be placed in the surgical opening and to receive the plurality of interchangeable seal elements.

11. The kit of claim 9, wherein the one or more mating elements further comprise a plurality of voids and tubes for forming a seal between an outside environment and a surgical location.

12. A method for accessing a surgical site, comprising:
   positioning a first seal element in an opening in tissue by mating the first seal element to the tissue or to a mating element of a retractor using a first mating element protruding from a first portion of an outer surface of the first seal element and configured to mate to and form a seal between the first seal element and the tissue, the first seal element having a second mating element protruding from a second portion of the outer surface thereof and an elongate sealable opening that has a length that is substantially similar to a length of the opening in tissue, the length of the elongate sealable opening and the length of the tissue opening being oriented in approximately the same direction when the first seal element is positioned in the opening in tissue;
   positioning at least one additional seal element in the opening in tissue, the additional seal element having a third mating element, a fourth mating element, and an elongate sealable opening, the third mating element protruding from a first portion of an outer surface of the additional seal element and being configure to mate to and form a seal between the second mating element and the third mating element; and the fourth mating element protruding from a second portion of the outer surface of the additional seal element and being configured to mate to and form a seal between fourth mating element and at least one of a mating element of an additional seal element, a mating element of a retractor, and tissue;
   inserting at least one surgical instrument into the sealable opening of the first seal element or the sealable opening of the at least one additional seal element; and
   manipulating the at least one surgical instrument while maintaining a seal between a body cavity adjacent to the opening in tissue and the outside environment.

13. The method of claim 12, further comprising insufflating a surgical site through at least one of the openings in first of the at least one seal element and the at least one additional seal element.

14. The method of claim 12, further comprising positioning a retractor in the opening in tissue, between the first seal element and the tissue, to form a seal between the retractor and the tissue and a seal between the retractor and the first seal element.

15. The method of claim 12, wherein the first portion of the outer surface of the first seal element includes a first sidewall and the second portion of the outer surface of the first seal element includes a second sidewall, the first and second sidewalls being elongate and approximately parallel to each other, and the first mating element protrudes from the first sidewall and the second mating element protrudes from the second sidewall, and wherein the first portion of the outer surface of the at least one additional seal element includes a third sidewall and the second portion of the outer surface of the at least one additional seal element includes a fourth sidewall, the third and fourth sidewalls being elongate and approximately parallel to each other, and the third mating element protrudes from the third sidewall and the fourth mating element protrudes from the fourth sidewall.

16. The kit of claim 9, wherein the one or more mating elements further comprise cooperating pliable component configured to form a seal therebetween.

17. The kit of claim 9, wherein the one or more mating elements further comprise cooperating rail and guide component configured to form a seal therebeweteen.

* * * * *